US010258221B2

(12) United States Patent
Fujimoto

(10) Patent No.: US 10,258,221 B2
(45) Date of Patent: Apr. 16, 2019

(54) OCULAR PORTION COUPLING APPARATUS

(71) Applicant: OLYMPUS CORPORATION, Tokyo (JP)

(72) Inventor: Yuji Fujimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 96 days.

(21) Appl. No.: 15/378,280

(22) Filed: Dec. 14, 2016

(65) Prior Publication Data

US 2017/0086655 A1 Mar. 30, 2017

Related U.S. Application Data

(63) Continuation of application No. PCT/JP2015/076518, filed on Sep. 17, 2015.

(30) Foreign Application Priority Data

Dec. 26, 2014 (JP) .................................. 2014-265541

(51) Int. Cl.
*A61B 1/04* (2006.01)
*A61B 1/00* (2006.01)
(Continued)

(52) U.S. Cl.
CPC ...... *A61B 1/00128* (2013.01); *A61B 1/00126* (2013.01); *A61B 1/00195* (2013.01);
(Continued)

(58) Field of Classification Search
CPC ............ A61B 1/00112; A61B 1/00121; A61B 1/00124; A61B 1/00126; A61B 1/00128
(Continued)

(56) References Cited

U.S. PATENT DOCUMENTS 4,611,888 A * 9/1986 Prenovitz ............... A61B 1/042
348/75
4,844,071 A * 7/1989 Chen ...................... A61B 1/042
600/112
(Continued)

FOREIGN PATENT DOCUMENTS

DE 44 25 705 A1 1/1996
JP H07-086590 B1 9/1995
(Continued)

OTHER PUBLICATIONS

Extended Supplementary European Search Report dated Jan. 15, 2018 in European Patent Application No. 15 87 2386.6.
(Continued)

*Primary Examiner* — Matthew J Kasztejna
(74) *Attorney, Agent, or Firm* — Scully, Scott, Murphy & Presser, P.C.

(57) ABSTRACT

An ocular portion coupling apparatus includes: a stepped pipe on which lock balls which are pressed against an eyepiece, are slidably arranged; and a rotation ring placed turnably on a ring placing surface, the rotation ring including a cam surface, wherein the stepped pipe includes convex pieces protruding outward from an outer circumferential surface of the large diameter portion, the convex pieces including one planes, the one planes and the ring placing surface sandwiching the rotation ring, and the rotation ring includes: axis direction grooves through which the convex pieces can pass; slide planes on which the one planes are slidably arranged; and restriction portions configured to prevent the convex pieces from dropping out through the axis direction grooves.

8 Claims, 13 Drawing Sheets

(51) Int. Cl.
*A61B 1/045* (2006.01)
*A61B 1/06* (2006.01)
*A61B 1/07* (2006.01)

(52) U.S. Cl.
CPC .............. *A61B 1/042* (2013.01); *A61B 1/045* (2013.01); *A61B 1/06* (2013.01); *A61B 1/07* (2013.01)

(58) Field of Classification Search
USPC ......... 600/112, 133, 137; 359/827; 403/348, 403/322.1; 385/25
See application file for complete search history.

(56) References Cited

U.S. PATENT DOCUMENTS

| | | | | |
|---|---|---|---|---|
| 4,969,450 A | * | 11/1990 | Chinnock | A61B 1/00195 600/109 |
| 5,156,141 A | * | 10/1992 | Krebs | G02B 23/2476 600/112 |
| 5,702,350 A | * | 12/1997 | Vry | A61B 1/00193 600/166 |
| 5,743,857 A | * | 4/1998 | Shinoda | A61B 5/02116 600/492 |
| 6,633,438 B2 | * | 10/2003 | Anhalt | A61B 1/00096 359/694 |
| 2006/0229495 A1 | | 10/2006 | Frith | |

FOREIGN PATENT DOCUMENTS

| | | |
|---|---|---|
| JP | H10-295638 A | 11/1998 |
| JP | H11-009549 A | 1/1999 |
| JP | H11-337846 A | 12/1999 |
| JP | 2004-147981 A | 5/2004 |
| JP | 2006-223477 A | 8/2006 |
| WO | 2011/137214 A1 | 11/2011 |

OTHER PUBLICATIONS

International Search Report dated Dec. 22, 2015 issued in International Application No. PCT/JP2015/076518.

* cited by examiner

OCULAR PORTION COUPLING APPARATUS

CROSS REFERENCE TO RELATED APPLICATION

This application is a continuation application of PCT/JP2015/076518 filed on Sep. 17, 2015 and claims benefit of Japanese Application No. 2014-265541 filed in Japan on Dec. 26, 2014, the entire contents of which are incorporated herein by this reference.

BACKGROUND OF THE INVENTION

1. Field of the Invention

The present invention relates to an ocular portion coupling apparatus in which an image pickup apparatus can be attached to and detached from an ocular portion of an observation apparatus by one touch.

2. Description of the Related Art

For example, in a scope that is one of observation apparatuses including optical viewing tube portions and ocular portions (also written as eyepieces), a camera head that is an image pickup apparatus may be attached to the ocular portion and used. In this case, the camera head is coupled to the eyepiece through an ocular portion coupling apparatus (also written as an eyepiece mount or a scope mount).

An eyepiece mount that can be attached to and detached from an eyepiece is illustrated in Japanese Patent Application Laid-Open Publication No. 2004-147981. A pressing portion pressed against a tapered portion of the eyepiece is provided on the eyepiece mount.

A scope mount including a scope mount main body, a scope lock, and a tightening ring is disclosed in Japanese Patent Application Laid-Open Publication No. 7-86590. A concave portion in which an eyepiece is fitted and mounted is formed on an inner circumference of the scope mount main body, and a locking body for locking an inclined portion (corresponding to the tapered portion in Japanese Patent Application Laid-Open Publication No. 2004-147981) of the eyepiece is provided on a front end portion. The tightening ring is rotated in a preset direction, and the locking body is pressed in a center axis direction by a thickness portion provided on an inner circumferential surface of the tightening ring.

An endoscope connection apparatus including a connection mechanism that allows sure attachment and detachment by one touch is disclosed in Japanese Patent Application Laid-Open Publication No. 10-295638. The endoscope connection apparatus includes: a scope mount connected to an ocular portion of a scope; and a camera adapter main body that is a connection apparatus main body detachably connected to the scope mount. A camera head main body is connected to an ocular portion of an endoscope through the endoscope connection apparatus. The scope mount includes: a mount portion that is a major diameter portion; and a convex portion protruding toward a back side of the mount portion, as shown in FIGS. 4(a) and (b) of Japanese Patent Application Laid-Open Publication No. 10-295638.

The scope mount disclosed in FIGS. 4(a) and (b) of Japanese Patent Application Laid-Open Publication No. 10-295638 mainly includes: an annular plate 1 shown in FIGS. 1A, 1B, and 2; a rotation ring 2 corresponding to the mount portion of Japanese Patent Application Laid-Open Publication No. 10-295638; a fixing component 3 including the convex portion of Japanese Patent Application Laid- Open Publication No. 10-295638; springs 4; spring fixing screws 5; and locking bodies 6.

Note that reference signs and names in parentheses in FIG. 1A are reference signs and names described in FIGS. 4(a) and (b) of Japanese Patent Application Laid-Open Publication No. 10-295638.

In FIG. 2, reference sign $1r$ denotes a ring portion. Reference sign $1c$ denotes a pair of convex portions protruding outward from an outer circumference of the ring portion $1r$. Reference sign $2a$ denotes plate placing surfaces, and convex portions $1c1$ and $1c2$ are arranged, respectively. Reference sign $2f$ denotes screw holes provided on the rotation ring 2. Reference sign $3a$ denotes a rotation ring placing surface, and a proximal end surface (not shown) of the rotation ring 2 is arranged. Reference sign $3f1$ denotes first screw holes provided on the fixing component 3, and reference sign $3f2$ denotes second screw holes provided on the fixing component 3. Reference sign $3h$ denotes pin holes, and the locking bodies 6 are arranged.

The scope mount is assembled as shown in FIGS. 3A to 3C.

First, the locking bodies 6 are arranged on the respective pin holes $3h$ formed on the fixing component 3.

Next, the fixing component 3 in which the locking bodies 6 are arranged in the pin holes $3h$ is covered with the rotation ring 2 as indicated by an arrow Y3A in FIG. 3A. Consequently, the rotation ring 2 is arranged on the rotation ring placing surface $3a$ provided on the fixing component 3.

In this arrangement state, the spring fixing screws 5 are screwed on the first screw holes $3f1$ of the fixing component 3 through hook holes $4h$ provided on one side of the springs 4 as indicated by arrows Y3B1 in FIG. 3B, and one end portions of the springs 4 are fixed to the fixing component 3. The spring fixing screws 5 are screwed on the screw holes $2f$ of the rotation ring 2 through the hook holes $4h$ provided on the other side of the springs 4 as indicated by arrows Y3B2 in FIG. 3B, and the other end portions of the springs 4 are fixed to the rotation ring 2.

Subsequently, the ring portion $1r$ of the annular plate 1 is arranged in a gap between the rotation ring 2 and the fixing component 3 as shown in FIG. 3C, and one convex portion $1c1$ and the other convex portion $1c2$ are arranged on the plate placing surfaces $2a$ of the rotation ring 2.

In this arrangement state, fixing screws 7 are screwed on the second screw holes $3f2$ of the fixing component 3 through relief holes $1h$ respectively provided on the convex portions $1c1$ and $1c2$, and the annular plate 1 is integrally fixed to the fixing component 3.

This prevents the rotation ring 2 from dropping out from the fixing component 3. The rotation ring 2 is turnably arranged between the convex portions $1c1$ and $1c2$ of the annular plate 1 fixed to the fixing component 3 and the rotation ring placing surface $3a$ of the fixing component 3.

According to the configuration, the rotation ring 2 of the scope mount is rotated and moved to a position shown in FIG. 4(a) by tension of the springs 4. Proximal end surfaces of the locking bodies 6 arranged on the pin holes $3h$ are pressed by a cam surface $2c$ provided on the rotation ring 2, and the locking bodies 6 are pushed out for a preset amount in a center axis direction. In this state, the scope mount is held and fixed to the ocular portion.

On the other hand, if the rotation ring 2 is rotated and operated in an arrow Y3B direction that is a counterclockwise direction against the tension of the springs 4 as shown in FIG. 3(B), the cam surface $3c$ gradually separates from the proximal end surfaces of the locking bodies 6 along with the rotation operation, and the pressing force is released.

As a result, the locking bodies 6 are in a slidable state in the pin holes 3h, and the locking bodies 6 can be retracted as indicated by a solid line. In the retractable state, the scope mount can be attached to the ocular portion, and the scope mount attached to the ocular portion can be removed.

SUMMARY OF THE INVENTION

An aspect of the present invention provides an ocular portion coupling apparatus including: a locking body, provided on an ocular portion of an observation apparatus, including a pressing portion pressed against a tapered surface at one end portion of the locking body; a fixing component including a slide hole on which the locking body is arranged slidably in a direction orthogonal to a center axis at a large diameter portion of the fixing component; and a rotation ring placed turnably on a ring placing surface provided on a circumferential surface side of the major diameter portion of the fixing component, the rotation ring including a cam surface rotated in one direction to gradually press another end portion of the locking body arranged in the slide hole to cause the pressing portion of the locking body to protrude for a preset amount from an inner circumferential surface of the large diameter portion to obtain a held and fixed state, the cam surface being rotated in another direction to allow the locking body to slide in the slide hole to obtain an attached and removed state, wherein the fixing component includes a convex piece protruding outward from an outer circumferential surface of the major diameter portion of the fixing component, the convex piece including one plane, the one plane and the ring placing surface sandwiching the rotation ring, and the rotation ring includes: an axis direction groove through which the convex piece can pass; a slide plane on which the one plane of the convex piece led out from the axis direction groove is slidably arranged; and a restriction portion configured to prevent the convex piece arranged on the slide plane from dropping out through the axis direction groove.

DETAILED DESCRIPTION OF THE PREFERRED EMBODIMENT(S)

Figure 1A:
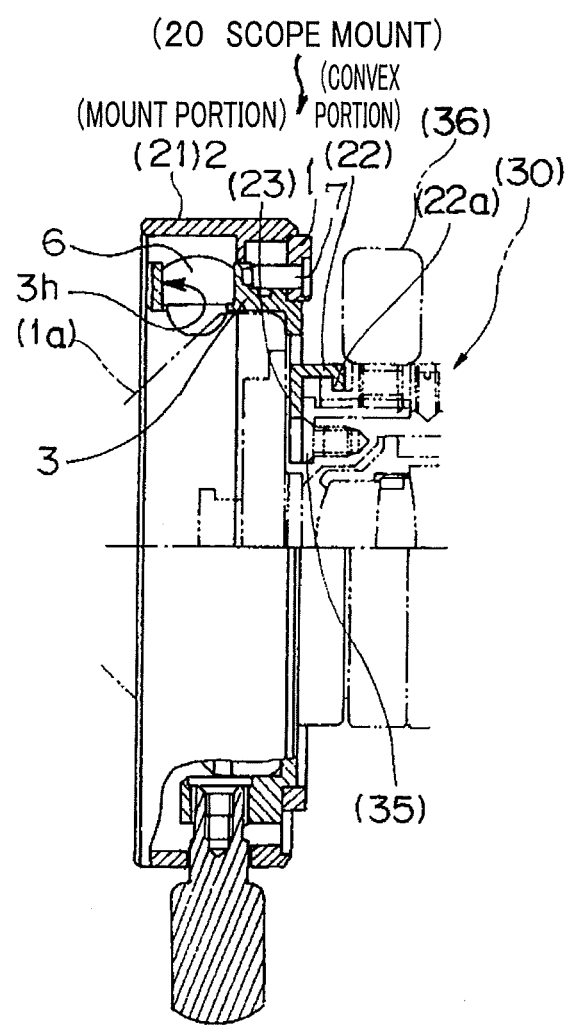
FIG. 1A is a diagram describing a configuration of a scope mount of Literature 3.
Figure 1B:
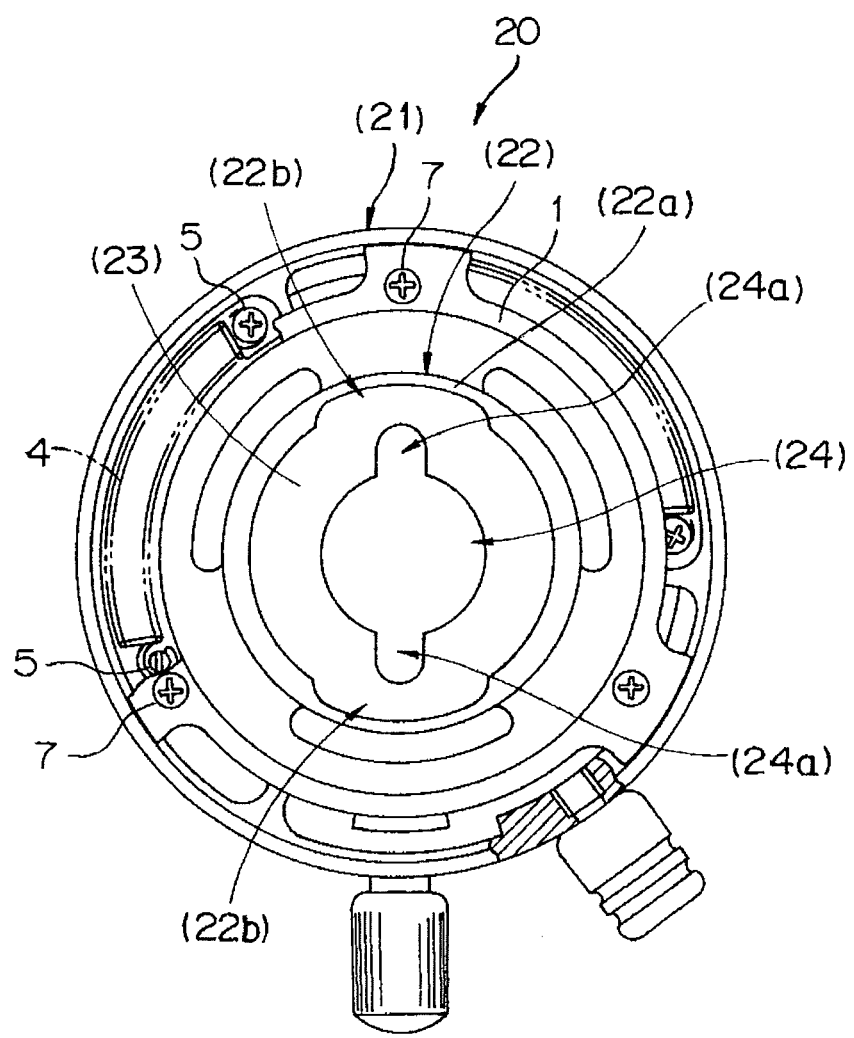
FIG. 1B is a diagram describing a configuration of the scope mount of Literature 3.
Figure 2:
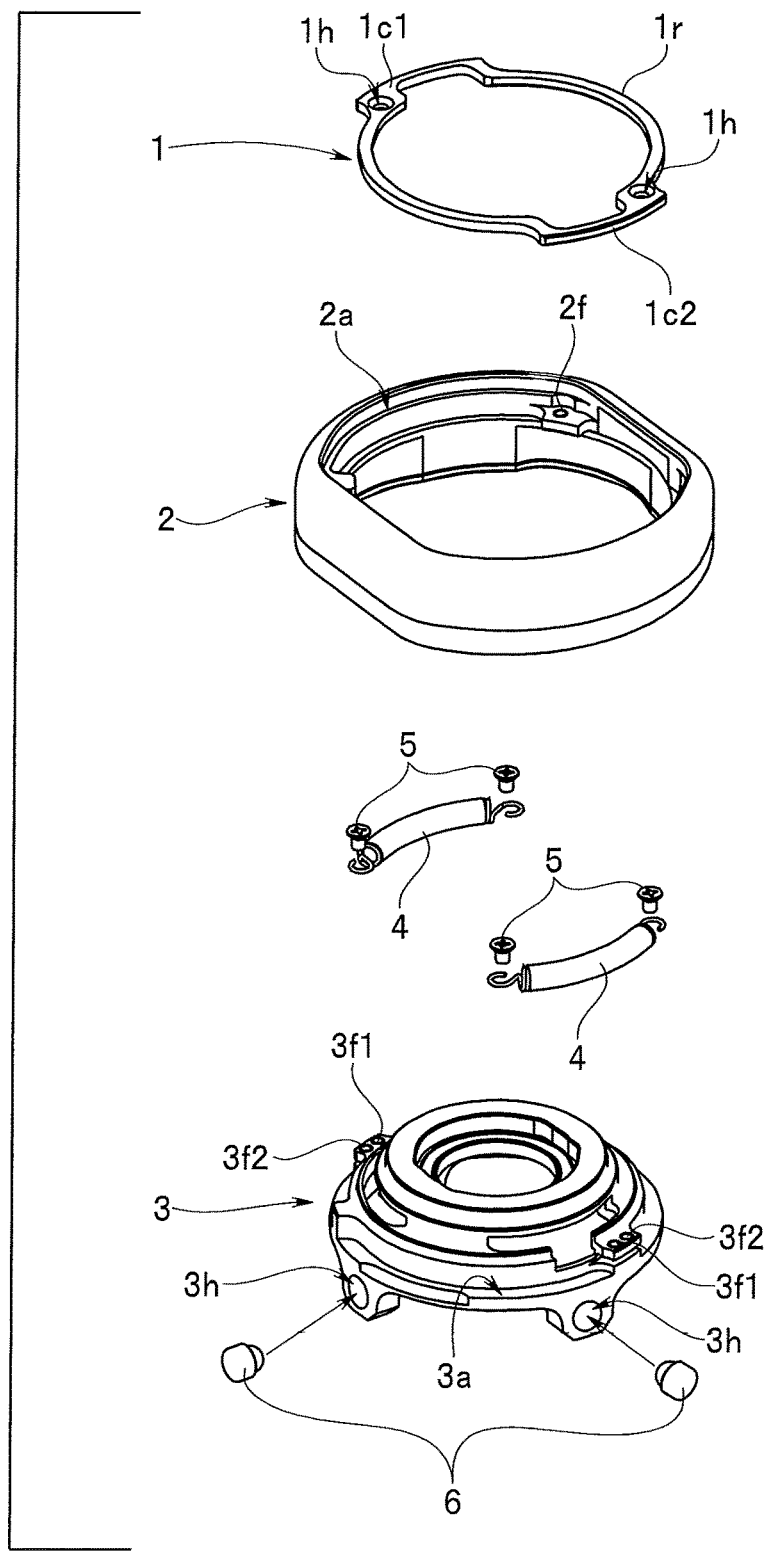
FIG. 2 is a diagram describing components included in the scope mount of Literature 3.
Figure 3A:
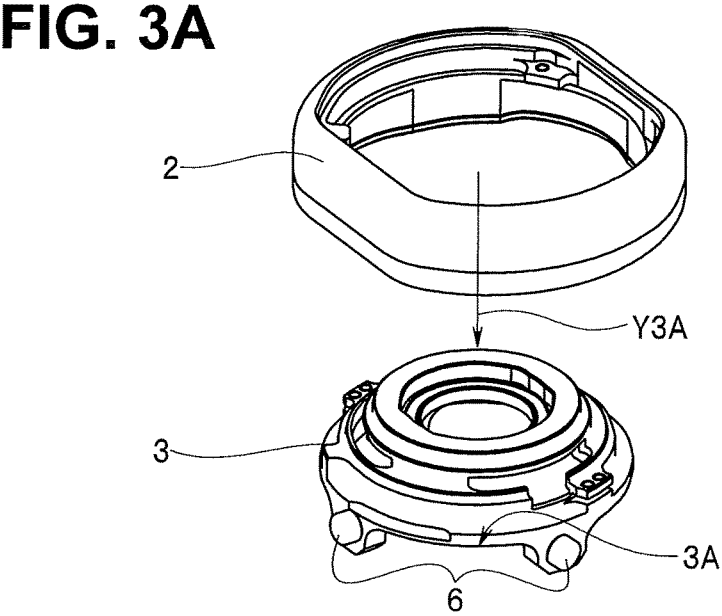
FIG. 3A is a diagram describing covering a rotation ring over a fixing component.
Figure 3B:
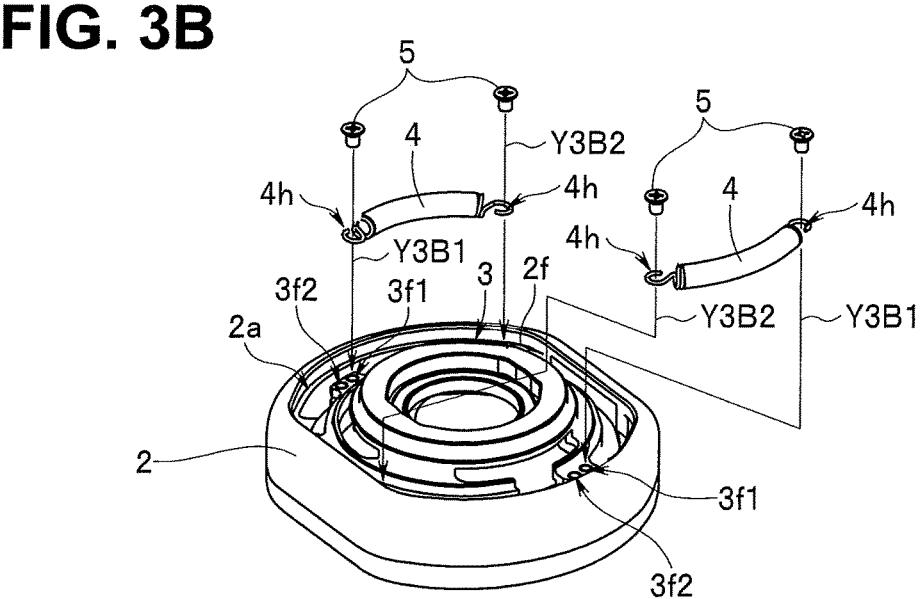
FIG. 3B is a diagram describing locating springs on the fixing component and the rotation ring in the state that the rotation ring covers over the fixing component.
Figure 3C:
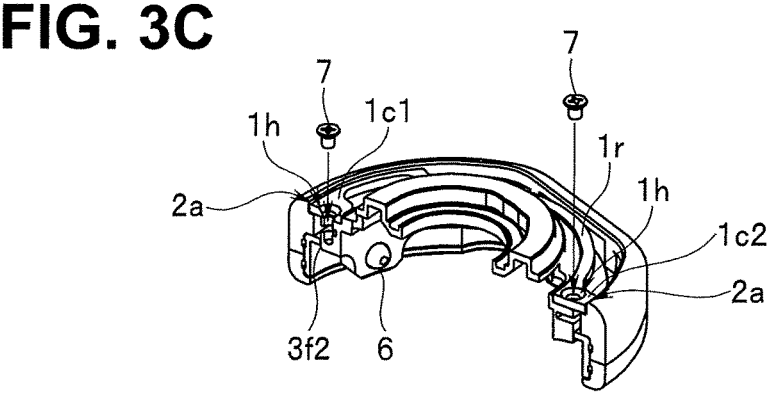
FIG. 3C is a diagram describing a state in which an annular plate is fixed to the fixing component, and the rotation ring is turnably arranged between convex portions of the annular plate and a rotation link placing surface.
Figure 4A:
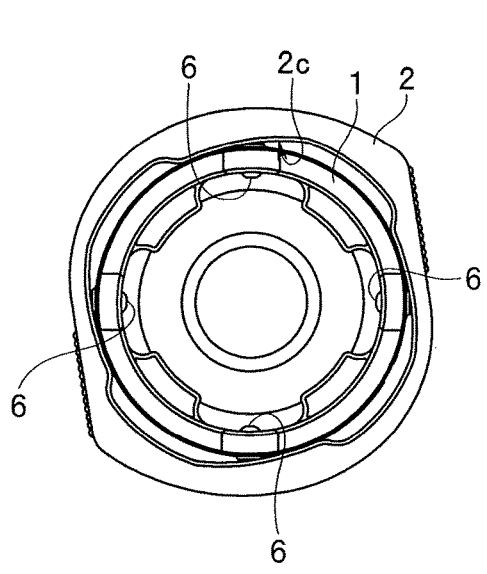
FIG. 4A is a diagram showing a state in which the scope mount can be held and fixed to an ocular portion and a state in which attachment of the scope mount to the ocular portion and removal of the scope mount attached to the ocular portion are possible.
Figure 4B:
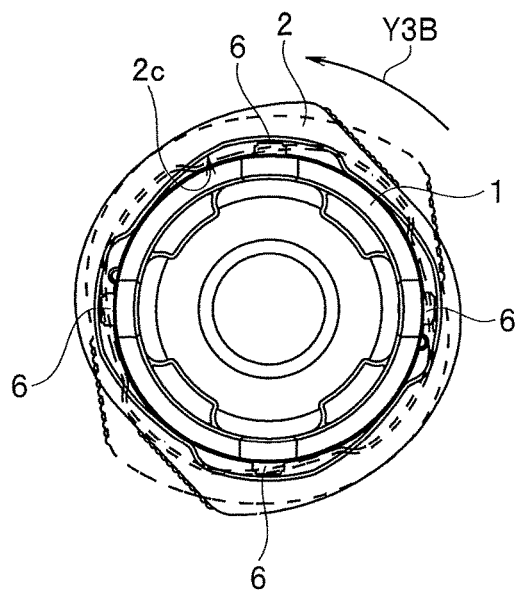
FIG. 4B is a diagram showing the state in which the scope mount can be held and fixed to the ocular portion and the state in which attachment of the scope mount to the ocular portion and removal of the scope mount attached to the ocular portion are possible.

Hereinafter, an embodiment of the present invention will be described with reference to the drawings.

Note that each drawing used in the following description is schematically illustrated, and a dimensional relationship, a scale, and the like of each member vary in each constituent element in order to illustrate each constituent element to an extent that allows recognizing the constituent element on the drawing. The present invention is not limited only to quantities of the constituent elements, shapes of the constituent elements, ratios of the sizes of the constituent elements, and relative positional relationships between respective constituent elements described in the drawings.

Figure 5:
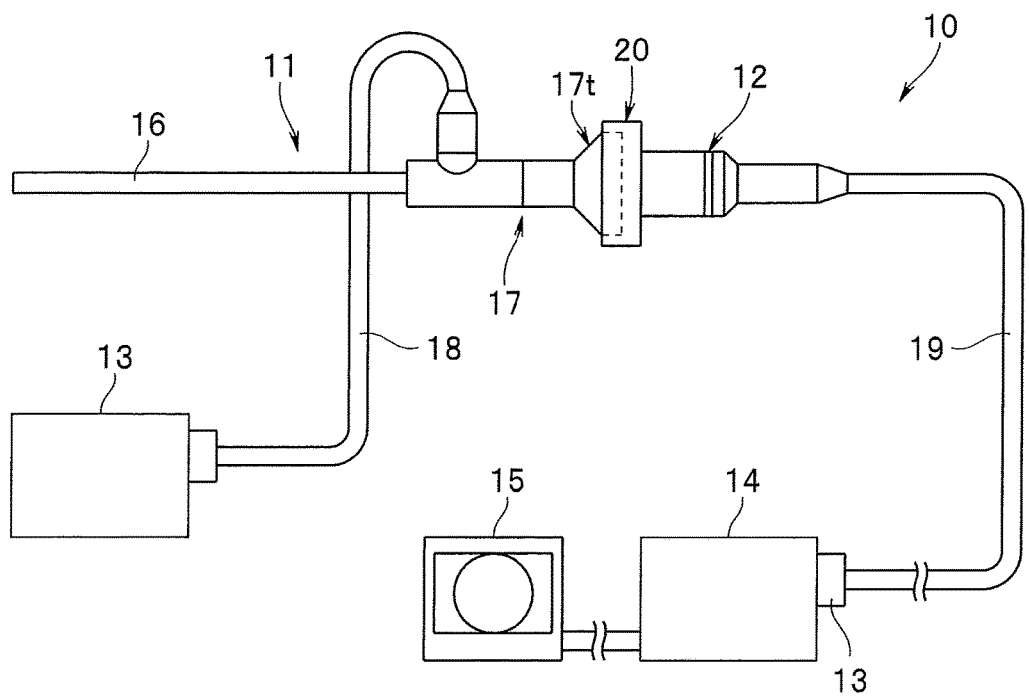
FIG. 5 is a diagram showing an endoscope system including an endoscope and a camera head that can be attached to and detached from an eyepiece through an ocular portion coupling apparatus.

Main parts of an endoscope system 10 shown in FIG. 5 include: an endoscope 11 that is an observation apparatus; a camera head 12 that is an image pickup apparatus; light source apparatuses 13 configured to supply illumination light; a camera control unit 14 configured to execute signal processing and the like; and a monitor 15. Reference sign 20 denotes an ocular portion coupling apparatus (hereinafter, written as a scope mount).

The camera head 12 can be connected to the endoscope 11 as described later. The illumination light of the light source apparatuses 13 is supplied to the endoscope 11. The camera control unit 14 applies signal processing to an image pickup signal transmitted from the camera head 12 and outputs a video signal after the signal processing to the monitor 15.

The endoscope 11 includes an elongated insertion portion 16 and an ocular portion (hereinafter, written as an eyepiece) 17. The eyepiece 17 has a diameter larger than the insertion portion 16, and a tapered surface portion 17t is provided on a proximal end side.

The camera head 12 can be connected to the eyepiece 17 through the scope mount 20. The scope mount 20 includes a rotation ring 30 that is a mount portion and a stepped pipe 40 that is a fixing component shown in FIG. 6.

Note that a proximal end side portion that is a small diameter portion of the stepped pipe 40 can be attached to and detached from the camera head 12.

Reference sign 18 of FIG. 5 denotes a light guide cable. The light guide cable 18 transmits the illumination light emitted from the light source apparatuses 13 to a light guide fiber bundle provided on the endoscope 11. The transmitted illumination light is applied toward a subject from an illumination window (not shown) provided on a distal end surface of the insertion portion 16.

An image in the subject illuminated by the illumination light is transmitted to the eyepiece 17 by, for example, a relay lens (not shown) provided in the insertion portion 16. As a result, a subject image can be observed through the eyepiece 17.

Reference sign 19 denotes a camera cable, and the camera cable 19 is extended from the camera head 12 and detachably connected to the camera control unit 14.

A configuration of the scope mount 20 will be described with reference to FIGS. 6 to 8.

Figure 6:
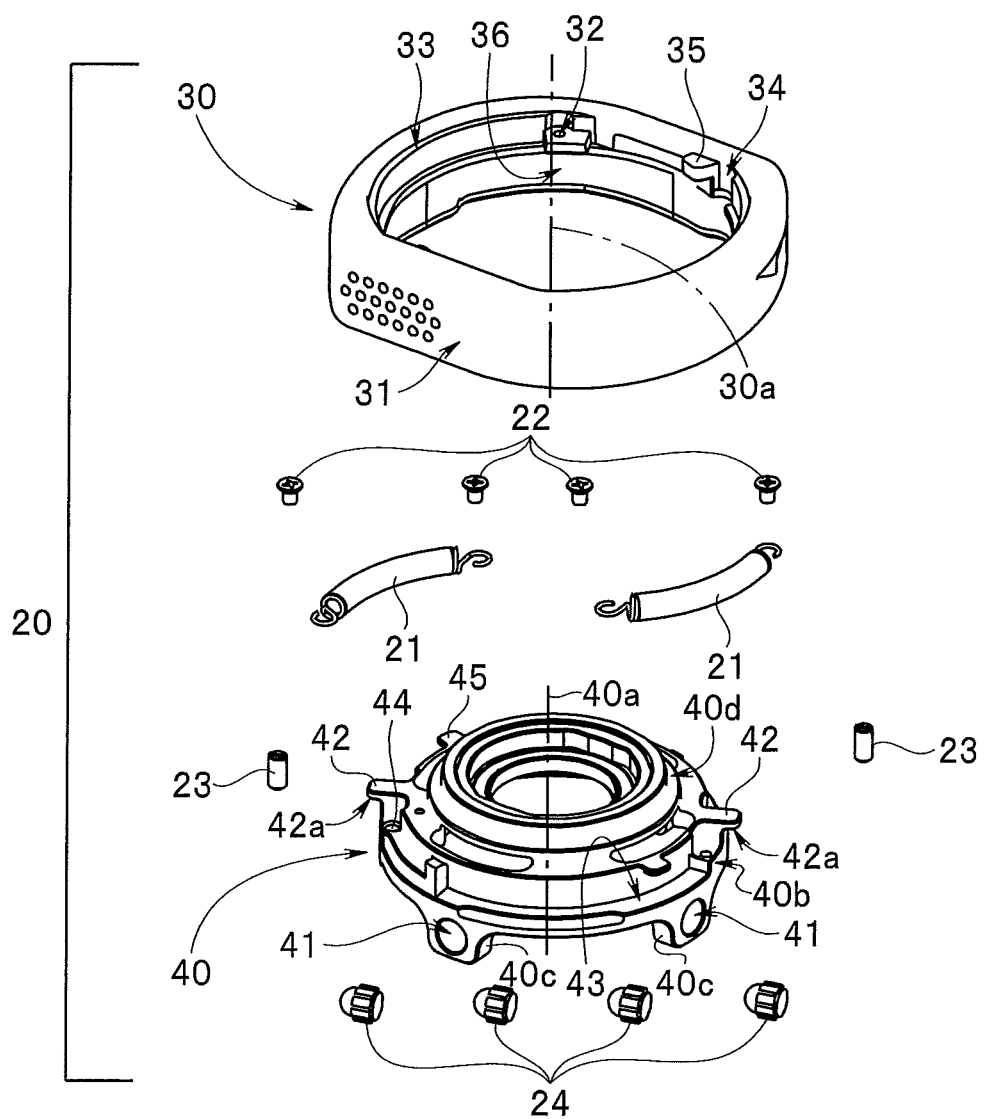
FIG. 6 is a diagram describing components included in a scope mount.

The scope mount 20 mainly includes the rotation ring 30 that is a mount portion and the stepped pipe 40 shown in FIG. 6 and further includes: springs 21 that are a pair of elastic members; a plurality of spring fixing screws 22; a pair of restriction male screws 23 that are restriction screw members configuring a restriction portion; and for example, four lock balls 24 that are locking bodies.

Figure 7A:
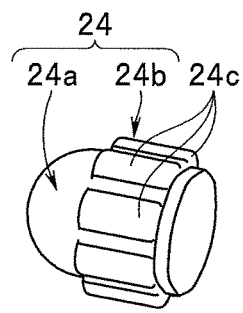
FIG. 7A is a diagram describing a lock ball.

The lock balls 24 are arranged on lock ball holes 42 of the stepped pipe 40. As shown in FIG. 7A, the lock ball 24 has a stepped shape including a small diameter portion 24a and a large diameter portion 24b. The small diameter portion 24a is a pressing portion pressed against the tapered surface portion 17t, and a distal end portion is hemispheric.

Figure 7B:
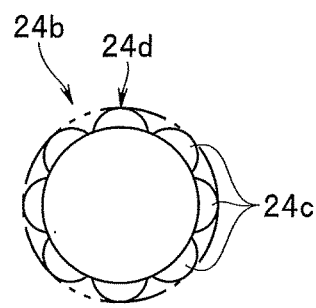
FIG. 7B is a diagram describing the lock ball.

As shown in FIGS. 7A and 7B, a plurality of projection portions 24c are aligned at preset intervals in a circumferential direction on an outer circumferential surface of the large diameter portion 24b. A cross-sectional shape of the projection portion 24c is, for example, semicircular and is elongated in an axis direction. The cross-sectional shape of the projection portion 24c is not limited to the semicircular shape, and a groove may be configured in a semicircular shape to provide a projection portion.

A proximal end surface of the large diameter portion 24b is an abutment surface where a cam surface 36 described later of the rotation ring 30 comes into contact.

Figure 7C:
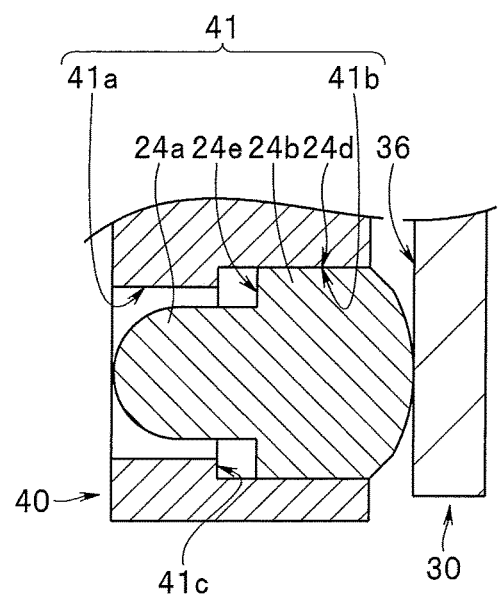
FIG. 7C is a diagram describing the lock ball.

In the present embodiment, the lock ball hole 41 is a through hole including an axis orthogonal to a center axis 40a and is a stepped hole including a minor diameter hole 41a and a major diameter hole 41b as shown in FIG. 7C.

The large diameter portion 24b is arranged in the major diameter hole 41b that is a slide hole, and an apex portion 24d of the projection portion 24c comes into linear contact with an inner circumferential surface of the major diameter hole 41b. The linear contact of the projection portion 24c of the large diameter portion 24b reduces sliding resistance, and a smooth sliding state can be obtained.

Reference sign 24e denotes a stepped surface of the small diameter portion 24a and the large diameter portion 24b, and reference sign 36 denotes the cam surface 36 provided on the rotation ring 30 and coming into contact with the proximal end surface of the large diameter portion 24b. The stepped surface 24e and the cam surface 36 prevent the lock ball 24 arranged in the lock ball hole 41 from dropping out from the inside of the hole.

Figure 8:
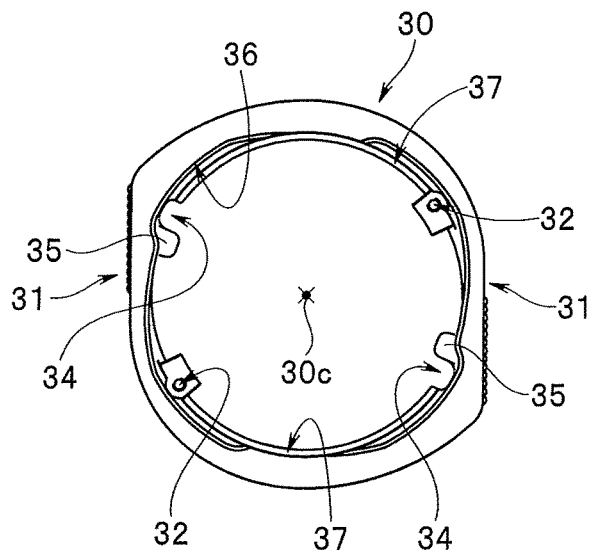
FIG. 8 is a view of a rotation ring from one surface side.

As shown in FIGS. 6 and 8, the rotation ring 30 of the scope mount 20 includes a pair of notched surfaces 31 on a circumferential surface side across the center axis 30a. The notched surfaces 31 are surfaces on which fingers of a user are arranged, and the notched surfaces 31 are held to rotate and operate the rotation ring 30.

On an inner circumferential surface side of the rotation ring 30, the pair of spring fixing screw holes 32, slide planes 33, a pair of axis direction grooves 34, a pair of restriction projection portions 35, the cam surface 36, and the like are provided.

The slide planes 33 are convex piece placing surfaces on which one planes 42a of convex pieces 42 described later provided on the stepped pipe 40 are slidably arranged. The axis direction grooves 34 are grooves formed along the center axis 30a of the rotation ring 30 and are grooves through which the convex pieces 42 can pass. The axis direction grooves 34 are formed to include groove openings at preset positions of the slide planes 33. The restriction projection portions 35 protrude in a center axis direction and are provided at preset positions adjacent to the groove openings of the axis direction grooves 34. The restriction projection portions 35 are restriction portions configured to restrict a rotation operation position of the rotation ring 30 relative to the stepped pipe 40. The cam surface 36 is the cam surface 36 coming into contact with proximal end surfaces of the lock balls 24 and is formed by changing the thickness.

As shown in FIG. 6, convex portions 40c provided with the lock ball holes 41 are provided on a large diameter portion 40b of the stepped pipe 40 of the scope mount 20. The convex pieces 42 protruding outward from the outer circumferential surface are also provided on the large diameter portion 40b.

The convex piece 42 has a preset thickness dimension and includes one plane 42a. The one plane 42a is a plane parallel to a rotation ring placing surface 43 on which the rotation ring 30 is placed. A distance from the one plane 42a to the rotation ring placing surface 43 is set to a preset dimension.

More specifically, in a state that a proximal end side surface 37 that is one surface of the rotation ring 30 is arranged on the rotation ring placing surface 43, one plane 42a of the convex piece 42 passing through the axis direction groove 34 is arranged and slidable on the slide plane 33 of the rotation ring 30 that is an opposite surface of the proximal end side surface.

Restriction screw holes 44 are formed at preset positions on sides of the convex pieces 42. The restriction screw holes 44 are female screw holes on which the restriction male screws 23 are screwed. The restriction male screws 23 screwed and fixed to the restriction screw holes 44 come into contact with the restriction projection portions 35. In the contact state, the restriction male screws 23 block at least part of the groove openings formed on the slide planes 33 of the axis direction grooves 34 to prevent the convex pieces 42 from passing through the axis direction grooves 34 again and dropping out from the rotation ring 30.

Note that reference sign 40d denotes a minor diameter convex portion. Reference sign 45 denotes a spring holder.

The scope mount 20 is assembled as shown in FIGS. 9A to 9G.

An assembler arranges the lock balls 24 in a predetermined state on the respective lock ball holes 41 provided on the stepped pipe 40.

Next, the assembler covers the rotation ring 30 over the stepped pipe 40 in which the lock balls 24 are arranged in the lock ball holes 41. In this case, the assembler causes the convex pieces 42 of the stepped pipe 40 to face the axis direction grooves 34 of the rotation ring 30. The assembler arranges the convex pieces 42 in the axis direction grooves 34 and then covers the stepped pipe 40 with the rotation ring 30 as indicated by an arrow Y9A of FIG. 9A.

Consequently, the proximal end side surface 37 of the rotation ring 30 is arranged on the rotation ring placing surface 43 provided on the stepped pipe 40. In this case, the convex pieces 42 are led from the groove openings of the axis direction grooves 34 as shown in FIG. 9B, and the convex pieces 42 are arranged adjacent to the restriction projection portions 35.

Figure 9A:
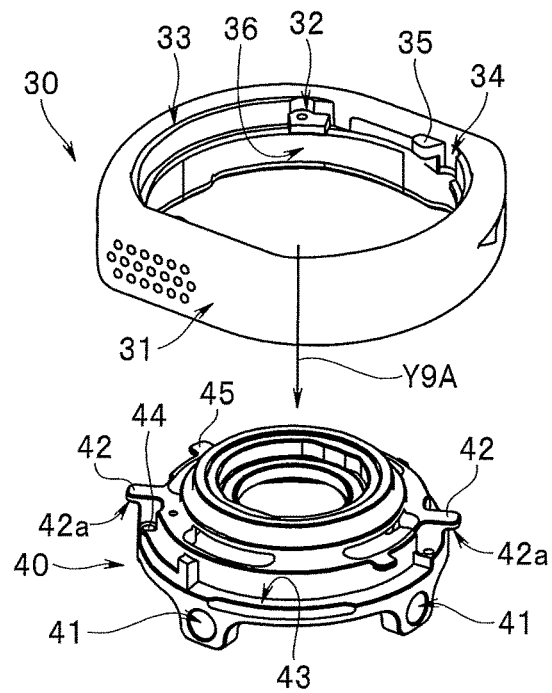
FIG. 9A is a diagram describing covering the rotation ring over an outer circumference side of a stepped pipe.
Figure 9B:
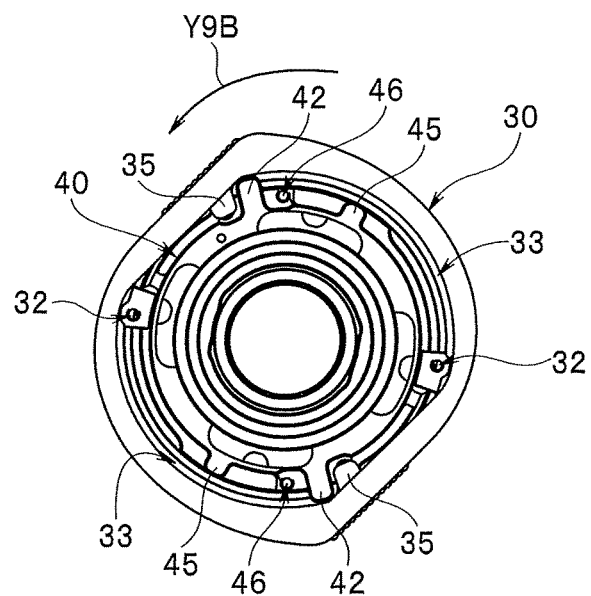
FIG. 9B is a diagram describing arranging convex pieces led from groove openings of axis direction groves on a slide plane.

Here, the assembler rotates the rotation ring 30 counterclockwise relative to the stepped pipe 40 as indicated by an arrow Y9B in FIG. 9B.

Figure 9C:
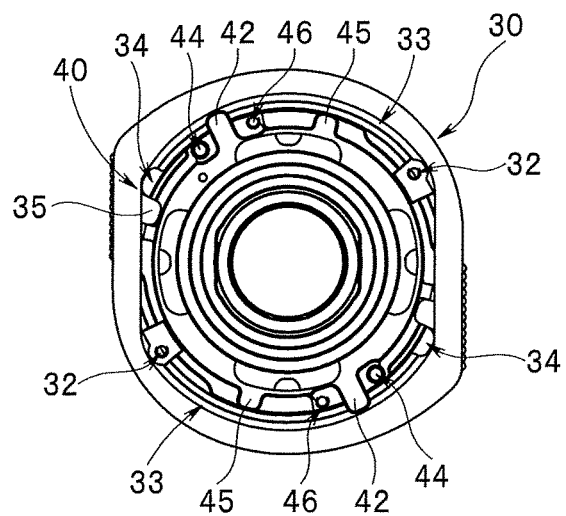
FIG. 9C is a diagram describing a state in which the convex pieces are arranged on the slide plane.
Figure 9D:
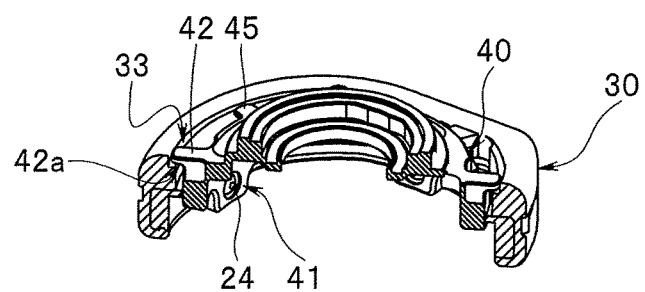
FIG. 9D is a cross-sectional view describing the state in which the convex pieces are being arranged on the slide plane.

Consequently, the one plane 42a of the convex piece 42 is arranged on the slide plane 33 as shown in FIGS. 9C and 9D, and the one plane 42a moves over the plane 33. As a result, the rotation ring 30 is in a state sandwiched by the rotation ring placing surface 43 of the stepped pipe 40 and the one plane 42a of the convex piece 42.

The axis direction grooves 34 show up along with the movement of the convex pieces 42, and the restriction screw holes 44 hidden by the restriction projection portions 35 show up.

Figure 9E:
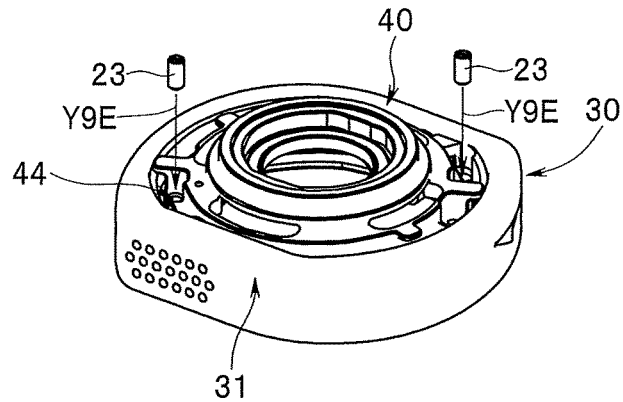
FIG. 9E is a diagram describing attaching restriction male screws to restriction screw holes.

Next, the assembler screws and fixes the restriction male screws 23 to the restriction screw holes 44 as indicated by arrows Y9E of FIG. 9E.

Figure 9F:
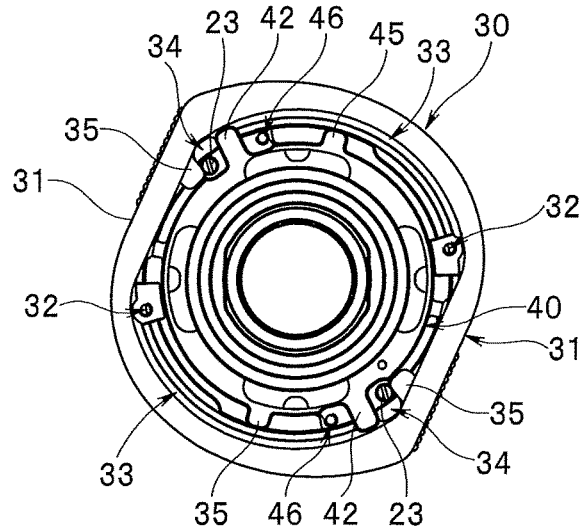
FIG. 9F is a diagram describing action in a state in which the restriction male screws and restriction projection portions are in contact with each other.

As a result, in a state that the restriction male screws 23 come into contact with the restriction projection portions 35 as shown in FIG. 9F, further movement of the convex pieces 42 toward the axis direction grooves 34 is restricted, and the convex pieces 42 are not arranged again on the groove openings of the axis direction grooves 34.

That is, this eliminates a malfunction that the convex pieces 42 pass again inside of the axis direction grooves 34 in the direction of the center axis 30a and that the rotation ring 30 drops out from the stepped pipe 40. The rotation ring 30 is arranged turnably relative to the stepped pipe 40. That is, the restriction male screws 23 and the restriction projection portions 35 serve as a restriction portion configured to restrict the rotation of the rotation ring 30 and a restriction portion configured to prevent the convex pieces from dropping out through the axis direction grooves 34.

Figure 9G:
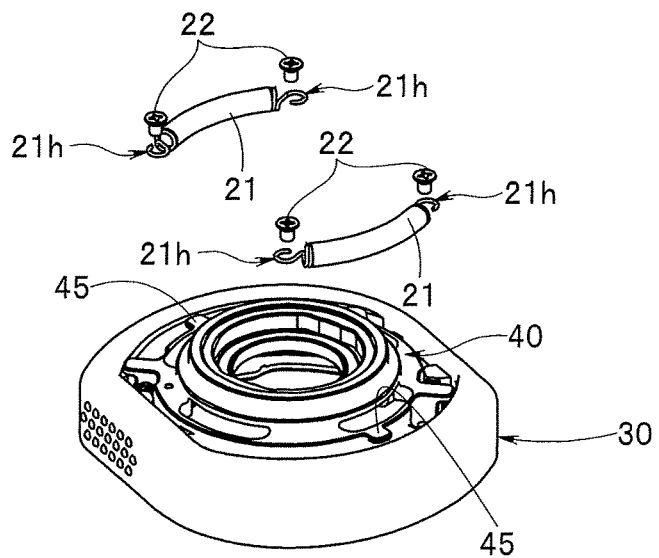
FIG. 9G is a diagram describing attaching springs to the rotation ring and the stepped pipe.
Figure 9H:
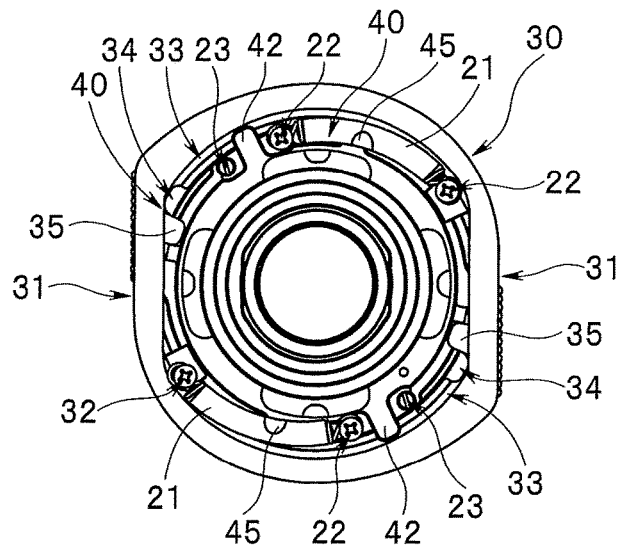
FIG. 9H is a diagram describing a state in which the springs are attached to the rotation ring and the stepped pipe.

In this state, the assembler arranges the springs 21 shown in FIGS. 9G and 9H under the lower side of the spring holder 45. The assembler screws the spring fixing screws 22 to spring screw holes 46 of the stepped pipe 40 through hook holes 21h provided on one side of the springs 21 and fixes one end portions of the springs 21 to the stepped pipe 40.

The spring fixing screws 22 are screwed on the spring fixing screw holes 32 of the rotation ring 30 through the hook holes 21h provided on the other side of the springs 21, and the other end portions of the springs 21 are fixed to the rotation ring 30.

As a result, the scope mount 20 is configured.

Figure 10A:
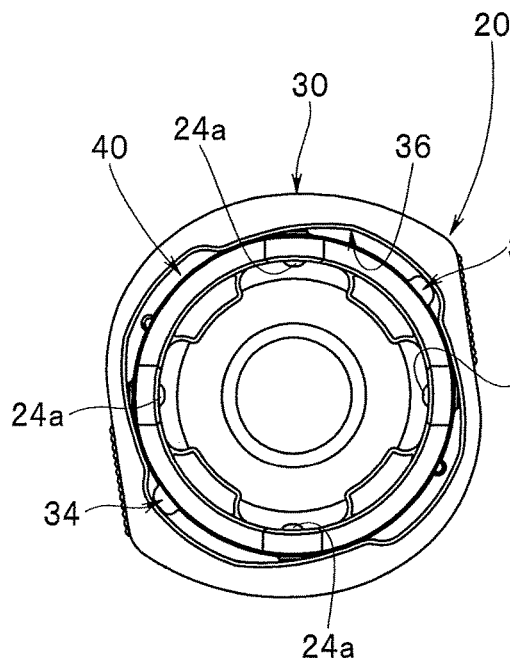
FIG. 10A is a diagram describing a state in which the scope mount can be held and fixed to the eyepiece, a state in which the scope mount can be attached to the eyepiece, and a state in which the scope mount can be removed from the eyepiece.

In the mount 20 configured in this way, the rotation ring 30 is moved by tension of the springs 21 as shown in FIG. 10A, and the proximal end surfaces of the lock balls 24 arranged on the lock ball holes 41 are pressed by the cam surface 36 of the rotation ring 30. The small diameter portions 24a of the lock balls 24 are pushed out for a preset amount in the center axis direction. In this state, the scope mount 20 is held and fixed to the eyepiece 17.

Figure 10B:
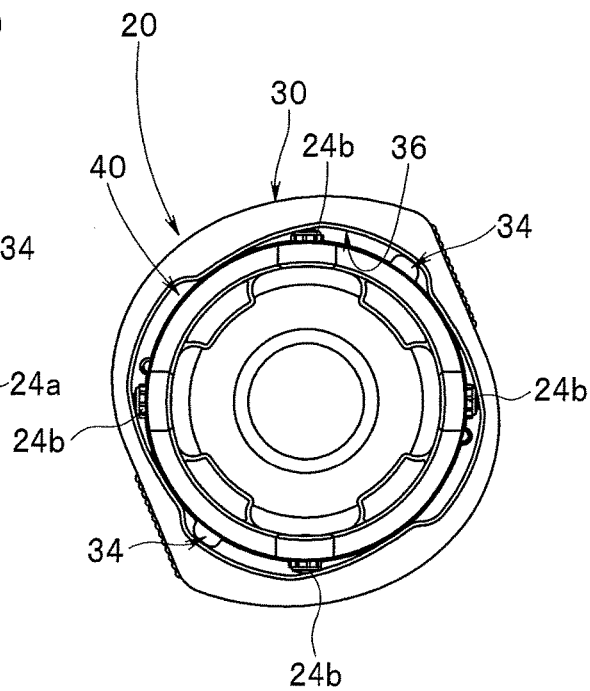
FIG. 10B is a diagram describing the state in which the scope mount can be held and fixed to the eyepiece, the state in which the scope mount can be attached to the eyepiece, and the state in which the scope mount can be removed from the eyepiece.

On the other hand, the rotation ring 30 is rotated and operated against the tension of the springs 21 as shown in FIG. 10B, and pressing force of the cam surface 36 pressing the proximal end surfaces of the large diameter portions 24b of the lock balls 24 is released. The restriction male screws 23 come into contact with the restriction projection portions 35 and reach a rotation operation end point position of the rotation ring 30.

In this case, the lock balls 24 are in a slidable state relative to the lock ball holes 41, and the lock balls 24 can be retracted without exposing the small diameter portions 24a as indicated by a solid line. In the retracted state, the scope mount 20 can be attached to the eyepiece 17 and removed from the eyepiece 17.

In this way, the convex pieces 42 are provided on the stepped pipe 40, and the axis direction grooves 34 are provided on the rotation ring 30. The slide planes 33 on which the one planes 42a of the convex pieces 42 are slidably arranged are provided.

As a result, the rotation ring 30 is turnably arranged relative to the stepped pipe 40 in the state that the one planes 42a are arranged on the slide planes 33.

In addition, the restriction screw holes 44 are provided on the stepped pipe 40, and the restriction projection portions 35 are provided on the rotation ring 30. The restriction male screws 23 are screwed and fixed to the restriction screw holes 44. As a result, in the state that the restriction male screws 23 are in contact with the restriction projection portions 35, the restriction male screws 23 block the groove openings of the axis direction grooves 34 to surely eliminate a malfunction that the rotation ring 30 drops out from the stepped pipe 40.

In the state that the malfunction that the rotation ring 30 drops outs from the stepped pipe 40 is eliminated, the springs 21 can be easily fixed.

As a result, the annular plate 1 configured to prevent the rotation ring 30 from dropping out from the stepped pipe 40 is unnecessary. The number of components can be reduced, and the assembly workability can be improved.

Note that in the present embodiment, the state that the restriction male screws 23 are in contact with the restriction projection portions 35 prevents the convex pieces 42 from reaching the groove openings provided on the slide planes 33 of the axis direction grooves 34, and at least part of the groove openings of 33 is blocked to prevent the rotation ring 30 from dropping out from the stepped pipe 40.

However, the configuration of preventing the convex pieces 42 from reaching again the groove openings provided on the slide planes 33 of the axis direction grooves 34 is not limited to the configuration in which the restriction male screws 23 are brought into contact with the restriction projection portions 35, and the following configuration is also possible.

Another configuration of the restriction portion will be described with reference to FIGS. 11A to 11C.

Figure 11A:
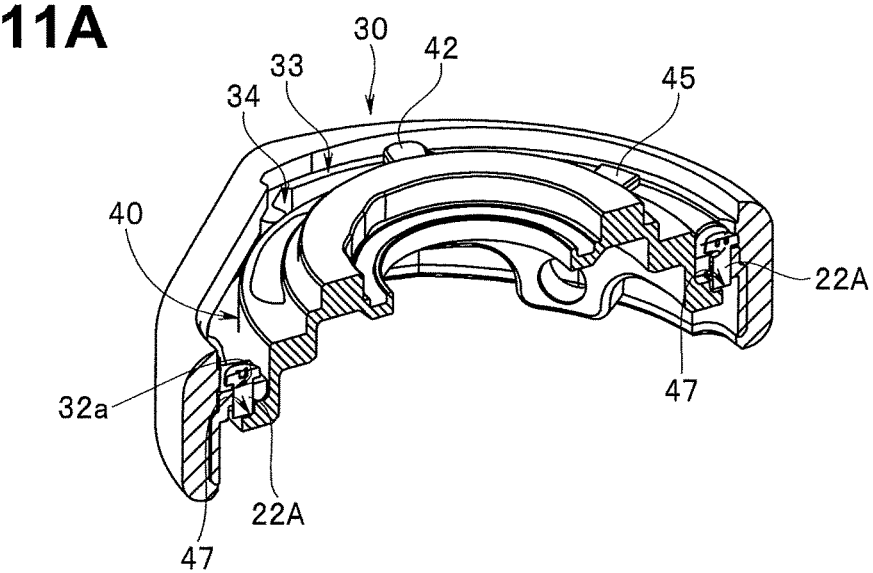
FIG. 11A is a diagram describing another example of configuration of a restriction portion, describing restriction male screws and restriction grooves included in the restriction portion.
Figure 11B:
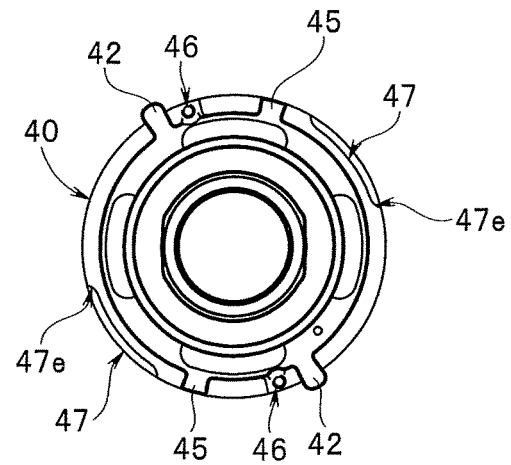
FIG. 11B is a diagram describing the restriction grooves and terminal portions provided on the restriction grooves.
Figure 11C:
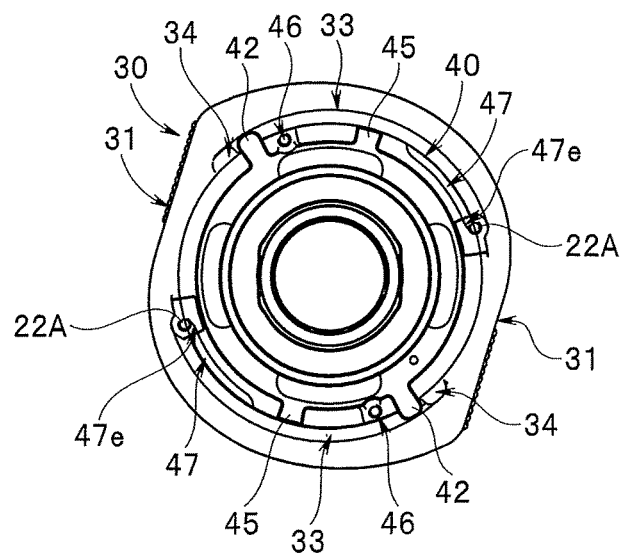
FIG. 11C is a diagram describing a state in which the scope mount can be attached to the eyepiece and a state in which the scope mount can be removed from the eyepiece.

As shown in FIGS. 11A and 11B, the restriction portion includes restriction male screws 22A and terminal portions 47e of restriction grooves 47. A length of the restriction male screws 22A is set such that the restriction male screws 22A protrude from the spring fixing screw holes 32 by a preset dimension. The restriction grooves 47 that are clearance grooves provided with distal end portions of the restriction male screws 22A protruding from the spring fixing screw holes 32 are formed on preset positions of the stepped pipe 40.

As shown in FIG. 11B, the terminal portions 47e of the restriction grooves 47 are restriction portions, and formation positions of the terminal portions 47e are positions preventing the convex pieces 42 from reaching the groove openings provided on the slide planes 33 of the axis direction grooves 34 when the distal end portions of the restriction male screws 22A come into contact with the terminal portions 47e as described above.

According to the configuration, the distal end portions of the restriction male screws 22A arranged on the restriction grooves 47 come into contact with the terminal portions 47e to restrict the convex pieces 42 from reaching the groove openings, and the malfunction that the rotation ring 30 drops out from the stepped pipe 40 is surely eliminated.

Other actions and effects are the same as in the embodiment described above.

The embodiment described above restricts the rotation operation end point position and restricts the convex pieces 42 from reaching the groove openings of the axis direction grooves 34 provided on the slide planes 33 when the rotation ring 30 is rotated and operated against the tension of the springs 21.

However, in the state that the rotation ring 30 is moved by the tension of the springs 21 to push out the small diameter portions 24a of the lock balls 24 for a preset amount in the center axis direction, the convex pieces 42 may be restricted from reaching the groove openings provided on the slide planes 33 of the axis direction grooves 34.

Another configuration of the restriction portion will be described with reference to FIGS. 12A and 12B.

Figure 12A:
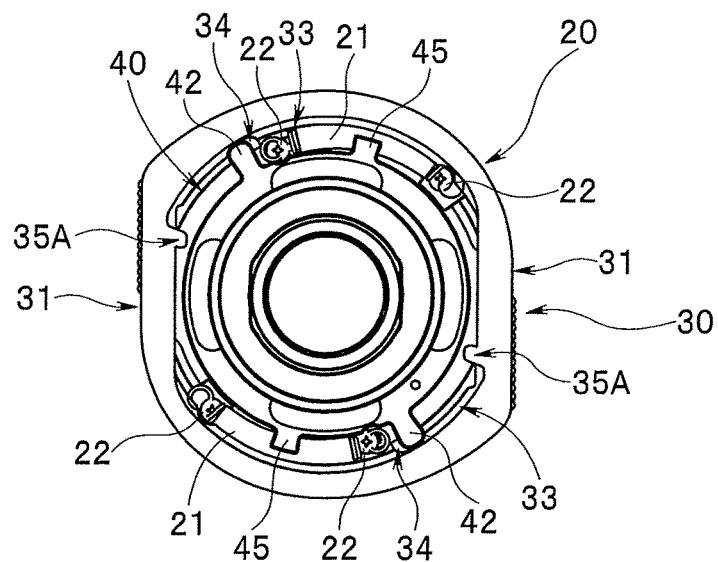
FIG. 12A is a diagram describing another configuration of the restriction portion, describing the springs as the restriction portion.
Figure 12B:
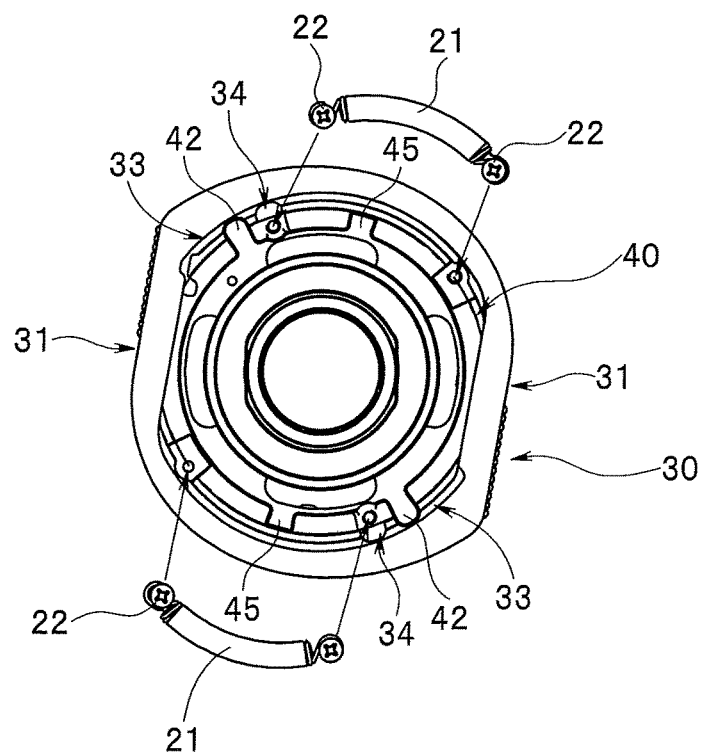
FIG. 12B is a diagram describing the springs and screw portions of the stepped pipe and screw portions of the rotation ring in which one end portions and other end portions of the springs are respectively fixed.

As shown in FIG. 12A, the restriction portion is the springs 21. In the closely contact state, the springs 21 restrict the convex pieces 42 from reaching the groove openings provided on the slide planes 33 of the axis direction grooves 34.

Note that reference sign 35A denotes restriction projection portions coming into contact with the convex pieces 42 when the rotation ring 30 reaches the rotation operation end point position.

When the rotation ring 30 is rotated and operated against the tension of the springs 21, the restriction projection portions 35A come into contact with the convex pieces 42, and the rotation ring 30 reaches the rotation operation end point position. In this case, as described above, the proximal end surfaces of the lock balls 24 are pressed by the cam surface 36, and the small diameter portions 24a of the lock balls 24 are pushed out for a preset amount in the center axis direction.

Other actions and effects are the same as in the embodiment described above.

The inventions described in the respective embodiments are not limited to the embodiments and the modified examples of the inventions, and various modifications can be carried out without departing from the scope of the inventions in an execution stage.

What is claimed is:

1. An ocular portion coupling apparatus configured to attach to and configure to detach from an ocular portion of an observation apparatus, the ocular portion coupling apparatus comprising:
   a fixing component having a stepped shape and including a small diameter portion and a large diameter portion, the fixing component being configured to be attached to and configured to be detached from the ocular portion;
   a ring placing surface provided on the large diameter portion;
   a slide hole formed in the large diameter portion in a central direction of the fixing component;
   a locking body disposed slidably in the slide hole;
   a pressing portion provided on one end portion of the locking body, the pressing portion being configured to be pressed against a tapered surface of the ocular portion;
   a rotation ring on the ring placing surface and turnable disposed on the fixing component, the rotation ring being configured to move the locking body in accordance with a rotation position of the rotation ring;
   a cam surface formed on an inner circumferential surface of the rotation ring, the cam surface being configured to move the locking body along the slide hole in accordance with rotation of the rotation ring; and
   a spring having one end portion fixed to the fixing component and another end portion fixed to the rotation ring;
   wherein the ocular portion coupling apparatus further comprises:
   a convex piece formed so as to protrude from an outer circumferential surface of the large diameter portion of the fixing component;
   an axis direction groove provided in the rotation ring, the axis direction groove being parallel to a rotation axis of the rotation ring, the axis direction groove configured so that the convex piece can pass through the axis direction groove upon a configuration of attachment and a configuration of detachment of the rotation ring to and from the fixing component;
   a restriction projection portion provided on the inner circumferential surface of the rotation ring to protrude in a direction of the rotation axis of the rotation ring to restrict a rotation operation position of the rotation ring with respect to the fixing component;
   a slide plane provided on the inner circumferential surface of the rotation ring, a plane of the convex piece configured to be slidably arranged on the slide plane; and
   a restriction screw member provided on the large diameter portion, the restriction screw member being configured to restrict the rotation position of the rotation ring with respect to the fixing component by the restriction projection portion being in contact with the restriction screw member, the restriction screw member being screwed in a vicinity of the convex piece so as to prevent the convex piece from passing through the axis direction groove.

2. The ocular portion coupling apparatus according to claim 1, wherein
a groove opening of the axis direction groove is formed on a preset position of the slide plane.

3. The ocular portion coupling apparatus according to claim 2, wherein
the restriction screw member is configured to be screwed and fixed to a restriction screw hole formed on a preset position of the fixing component; and
the restriction projection portion is provided on a preset position of an inner circumferential surface of the rotation ring and protruding in a rotation axis direction of the rotation ring.

4. The ocular portion coupling apparatus according to claim 3, wherein
the restriction screw member blocks at least part of the groove opening formed on the slide plane of the axis direction groove.

5. The ocular portion coupling apparatus according to claim 3, wherein
the restriction screw member and the restriction projection portion are configured to contact each other in the attached and removed state in which the locking body is slidable in the slide hole.

6. The ocular portion coupling apparatus according to claim 2, wherein a restriction male screw is screwed on a spring fixing screw hole provided on the rotation ring, a length of the restriction male screw being set to a length such that a distal end portion protrudes from the spring fixing screw hole by a predetermined dimension; and a clearance groove is provided on the fixing component and comprising a terminal portion where the distal end portion of the restriction male screw protruding from the spring fixing screw hole comes into contact.

7. The ocular portion coupling apparatus according to claim 6, wherein the distal end portion of the restriction male screw and the terminal portion of the clearance groove come into contact with each other in an attached and removed state in which the locking body is slidable in the slide hole.

8. The ocular portion coupling apparatus according to claim 2, wherein a tension of the spring brings the cam surface of the rotation ring into contact in a held and fixed state in which a distal end portion of the locking body arranged in the slide hole is protruded for a preset amount from an inner circumferential surface of the large diameter portion, thereby preventing the convex piece from dropping out through the groove opening formed on the slide plane of the axis direction groove.

* * * * *

UNITED STATES PATENT AND TRADEMARK OFFICE
CERTIFICATE OF CORRECTION

PATENT NO. : 10,258,221 B2
APPLICATION NO. : 15/378280
DATED : April 16, 2019
INVENTOR(S) : Yuji Fujimoto Page 1 of 1

It is certified that error appears in the above-identified patent and that said Letters Patent is hereby corrected as shown below:

In the Claims

Column 10, Claim 1, Line 30 should read:
a rotation ring on the ring placing surface and turnably Signed and Sealed this
Sixth Day of August, 2019

Andrei Iancu
*Director of the United States Patent and Trademark Office*